US00PP24260P3

(12) United States Plant Patent
Korlipara

(10) Patent No.: US PP24,260 P3
(45) Date of Patent: Feb. 25, 2014

(54) ***LEUCANTHEMUM* PLANT NAMED 'BRIDAL BOUQUET'**

(50) Latin Name: *Leucanthemum×superbum*
Varietal Denomination: Bridal Bouquet

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 226 days.

(21) Appl. No.: 13/200,289

(22) Filed: Sep. 21, 2011

(65) Prior Publication Data

US 2013/0074234 P1 Mar. 21, 2013

(51) Int. Cl.
*A01H 5/00* (2006.01)

(52) U.S. Cl.
USPC ..... Plt./285

(58) Field of Classification Search
USPC ..... Plt./285, 284, 263.1
See application file for complete search history.

*Primary Examiner* — Kent L Bell
(74) *Attorney, Agent, or Firm* — Klarquist Sparkman, LLP

(57) ABSTRACT

A new and distinct *Leucanthemum* plant named 'Bridal Bouquet' characterized by daisy type inflorescences that are lightly ruffled and double, with yellow ray florets in the young inflorescences, numerous white ray florets around a large gold disc, excellent bloom size, a very low, compact habit, and excellent vigor.

1 Drawing Sheet

Botanical denomination: *Leucanthemum×superbum.*
Variety designation: 'Bridal Bouquet'.

The present invention relates to a new and distinct cultivar of *Leucanthemum* and given the cultivar name 'Bridal Bouquet'. *Leucanthemum* is in the family Asteraceae. This new cultivar originated from a controlled cross between unknown, unnamed, proprietary *Leucanthemum×superbum* seedlings. The seed of many crosses was massed so the exact parents are unknown.

Compared to *Leucanthemum* 'Esther Read', an unpatented plant, the new cultivar has double inflorescences rather than crested anemone type inflorescences and has yellow rather than white immature inflorescences.

Compared to *Leucanthemum* 'Daisy Duke', U.S. Plant Pat. No. 21,914, the new cultivar is shorter, with yellow rather than white immature inflorescences, and has double rather than single inflorescences.

This new *Leucanthemum* cultivar is distinguished as unique with its:

1. daisy type inflorescences that are lightly ruffled and double,
2. yellow ray florets in the young inflorescences,
3. numerous white ray florets around a large gold disc,
4. excellent bloom size,
5. a very low, compact habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 1 year old plant growing in the ground in full sun in the trial field in mid July in Canby, Oreg.

DETAILED PLANT DESCRIPTION

The following is a detailed description of the new *Leucanthemum* cultivar based on observations of 2-year-old specimens growing in two gallon containers in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:
- *Type.*—Herbaceous perennial.
- *Hardiness.*—USDA Zones 5 to 9.
- *Size.*—38 cm wide and 25 cm tall to top of inflorescences.
- *Form.*—Basal clump.
- *# crowns.*—15.
- *Vigor.*—Excellent.

Stem (flowering):
- *Type.*—Ascending strongly upright with thick, strong stems.
- *Number of stems.*—About 15 stems from the crown, each flowering with 1 to 3 flowers per stem (older plants have up to 7 flowers per stem).
- *Size.*—Grows to about 21 cm tall to a terminal inflorescence and 9 mm wide at base.
- *Internode length.*—2 to 2.5 cm.
- *Surface texture.*—Pubescent.
- *Color.*—Yellow Green 146B except on older stems at the base where Greyed Purple 187B.

Leaf (basal):
- *Type.*—Simple.
- *Shape.*—Oblanceolate.

*Arrangement.*—Basal.
*Size.*—Grows to 20 cm long and 3 cm wide.
*Margins.*—Coarsely serrate.
*Apex.*—Acute.
*Base.*—Attenuate.
*Surface texture.*—Pubescent on both sides.
*Venation.*—Pinnate.
*Petiole.*—Sessile.
*Color.*—Topside Green 137B, bottom side Green 137C.

Leaf (stem):
*Type.*—Simple.
*Shape.*—Lanceolate.
*Arrangement.*—Alternate.
*Blade size.*—Grows to 8.5 cm long and 15 mm wide.
*Margins.*—Coarsely serrate.
*Apex.*—Acute.
*Base.*—Clasping.
*Surface texture.*—Pubescent on both sides.
*Venation.*—Pinnate.
*Petiole.*—Sessile.
*Color.*—Topside Green 137B, bottom side Green 137C.

Inflorescence:
*Type.*—Composite on terminal stalked heads.
*Number of inflorescences per plant.*—About 21.
*Size.*—Grows to 8.5 cm wide and 3.5 cm deep.
*Form.*—Ray florets are held horizontally with the bottom layers reflexed downwards, mature disc is rounded.
*Immature inflorescence* (*bud*).—4.5 cm wide and 2.5 cm deep, ray florets held vertically and cupped inwards, Yellow 4A overall.
*Ray florets.*—With 1 pistil and no stamen, about 90 in number (about 15 smaller size near the disc florets), mostly oblong, tip retuse to 3 lobed, margins entire, base obtuse, average size 3 cm long and 1 cm wide, glabrous on both sides; top and bottom side Yellow 5D when young and fully open maturing to White 155C with base Yellow Green 144B; pistil 6 mm long, ovary 0.5 mm long, Yellow Green 145D, style 5 mm long, Yellow 13D, 2 branched stigma 0.5 mm long, Yellow 13A.
*Disc.*—Slightly concave becoming convex, becoming 14 mm deep and 38 mm wide with maturity, Yellow Orange 17B.
*Disc florets.*—About 600 in number, each 7 mm long and 1.5 mm wide; corolla tubular campanulate, 6 mm long and 1.5 mm wide, 5 lobed, glabrous, Yellow 13A on top half and Yellow Green 145A on the bottom half; pistil 1, 7 mm long, ovary 1.5 mm long and Yellow Green 145C, style 5 mm long, Yellow 13D, 2 branched stigma 0.5 mm long, Yellow 13A; stamen 5 in number, 4 mm long, filaments 2 mm long, Yellow Green 150D, anthers 2 mm Yellow Orange 17A, pollen in moderate amount, Yellow Orange 21A.
*Involucral bracts.*—About 80 in number, in 3 imbricate whorls, area 3.5 cm wide and 9 mm deep, lobes lanceolate in shape, grow to 8 mm long and 2 mm wide, Yellow Green 147B to 147A, margin thin and somewhat transparent, Greyed Purple 187A, tip acute, glabrous.
*Receptacle.*—Grows to 23 mm wide and 4 mm deep, Yellow Green 145C.
*Bloom period.*—June through October in Canby, Oreg.
*Fragrance.*—Slight.
*Lastingness.*—Each inflorescence lasts about two weeks in Canby, Oreg.

Seeds: None seen.
*Fertility.*—Low.

Disease and pests: *Leucanthemum* are susceptible to aphids and leaf spots. These have not been observed on plants grown under commercial conditions in Canby, Oreg. No resistances are known.

I claim:

1. A new and distinct *Leucanthemum* plant as herein illustrated and described.

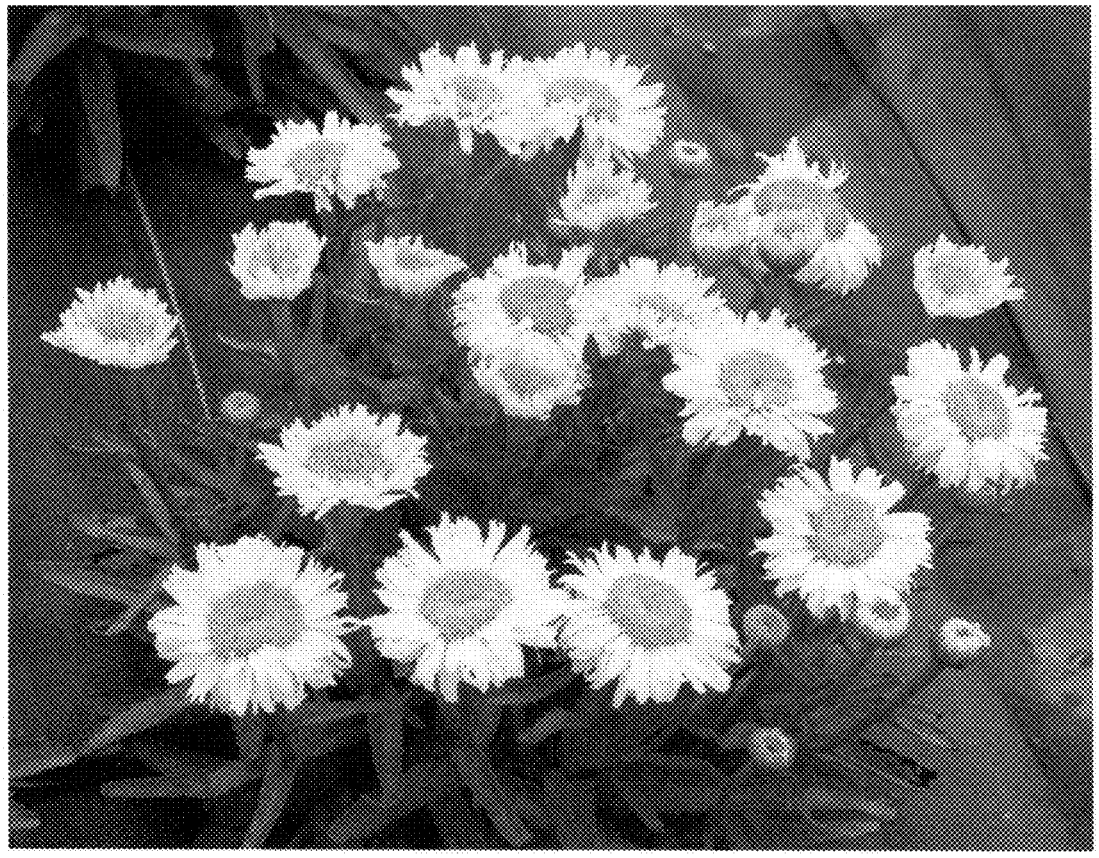

* * * * *